US012797096B2

(12) United States Patent
Perez Serranos et al.

(10) Patent No.: US 12,797,096 B2
(45) Date of Patent: Nov. 17, 2026

(54) THROMBOTIC MATERIAL EXTRACTION

(71) Applicant: LIFE VASCULAR DEVICES BIOTECH, S.L., Sant Vicenç Dels Horts (ES)

(72) Inventors: Isabel Perez Serranos, Castelldefels (ES); Marta Duran Priu, Sant Boi de Llobregat (ES); Luis Duocastella Codina, Santa Coloma de Cervelló (ES); Juan Miguel Macho Fernandez, Barcelona (ES); Enrique Castro Reyes, Majadahonda (ES); Alejandro González García, Seville (ES); Aina Laguarta Alapont, Manresa (ES)

(73) Assignee: LIFE VASCULAR DEVICES BIOTECH, S.L., Sant Vicenç Dels Horts (ES)

( * ) Notice: Subject to any disclaimer, the term of this patent is extended or adjusted under 35 U.S.C. 154(b) by 338 days.

(21) Appl. No.: 18/717,523

(22) PCT Filed: Dec. 7, 2022

(86) PCT No.: PCT/EP2022/084865
§ 371 (c)(1),
(2) Date: Jun. 7, 2024

(87) PCT Pub. No.: WO2023/104923
PCT Pub. Date: Jun. 15, 2023

(65) Prior Publication Data

US 2025/0049457 A1 Feb. 13, 2025

(30) Foreign Application Priority Data

Dec. 9, 2021 (EP) .................................... 21383118

(51) Int. Cl.
*A61B 17/221* (2006.01)
*A61B 17/22* (2006.01)

(52) U.S. Cl.
CPC ...................... *A61B 17/221* (2013.01); *A61B 2017/22067* (2013.01); *A61B 2017/22079* (2013.01)

(58) Field of Classification Search
CPC ................ A61B 17/221; A61B 17/22; A61B 2017/22067; A61B 2017/22079; A61B 2017/2215; A61B 2217/005
See application file for complete search history.

(56) References Cited

U.S. PATENT DOCUMENTS 10,485,952 B2 11/2019 Garrison et al.
2006/0058837 A1* 3/2006 Bose ..................... A61B 17/22 606/200
2021/0402157 A1* 12/2021 Keating .......... A61M 25/10181

OTHER PUBLICATIONS

International Search Report and Written Opinion of International Application No. PCT/EP2022/084865, dated Mar. 2, 2023, 13 pages.

* cited by examiner

*Primary Examiner* — Dung T Ulsh
(74) *Attorney, Agent, or Firm* — Chrisman Gallo Tochtrop LLC

(57) ABSTRACT

A catheter for extracting thrombotic material from a head blood vessel. The catheter includes a suction sheath to extract the thrombotic material from a distal side to a proximal side of the catheter; an inflation sheath to feed an inflatable balloon to occlude the blood vessel in an inflated state; a tubular extension extending beyond the distal end of the inflation sheath, the extension being defined such that a distal tip of the extension is placed downstream the ophthalmic segment when the distal end of the inflation sheath is placed upstream the ophthalmic segment. A method for extracting thrombotic material from a head blood vessel is provided as well.

19 Claims, 7 Drawing Sheets

THROMBOTIC MATERIAL EXTRACTION

CROSS-REFERENCE TO RELATED APPLICATIONS

This is a National Stage application of PCT International Application PCT/EP2022/084865, filed on Dec. 7, 2022, which claims the benefit of European Patent Application EP21383118.3 filed on Dec. 9, 2021, both of which are incorporated herein by reference in their entirety.

The present disclosure generally relates to devices and methods for extracting thrombotic material, and more specifically, to a catheter for extracting thrombotic material from a head blood vessel, methods and systems.

BACKGROUND

A stroke is a medical disorder in which the blood supply to a part of the brain is interrupted. The concerned part of the brain is deprived of oxygen and nutrients. The stroke is a cerebrovascular disease that may cause severe health problems and even cause death.

There are two types of strokes: ischemic in which the blood flow through a supply vessel to the brain is blocked, and hemorrhagic due to bleeding in the brain. The ischemic stroke may be caused by a blood clot or thrombotic material that blocks or plugs a blood vessel in the brain.

A large number of ischemic strokes occur in the area of the middle cerebral artery. Thrombotic material, e.g. a thrombus, can be located within the middle cerebral artery. A treatment procedure consists in removing the thrombus from the middle cerebral artery. In recent years, procedures have been developed that involve the use of catheters that may be inserted or advanced through a blood vessel into the middle cerebral artery.

The catheters may have inflatable devices that temporarily block the blood circulation upstream the blood vessel to facilitate the removal of thrombotic material downstream the blood vessel.

Although catheters offer a less traumatic solution than other older surgical procedures, catheter inflatable devices may damage the vessel wall and may cause bleeding. The latter is particularly severe when the brain area is involved.

Even if the catheter procedure is performed by significantly specialized personnel, the condition of the vessel walls may make it inadvisable to perform the procedure because of the risk of damaging the vessel.

Therefore, there is still a need for a catheter, methods and systems to extract thrombotic material from a head blood vessel that may resolve at least some of the aforementioned problems.

SUMMARY

In a first aspect, a catheter for extracting thrombotic material from a head blood vessel is provided. The catheter comprises a suction sheath to extract the thrombotic material from a distal side to a proximal side of the catheter, and an inflation sheath to feed an inflatable balloon to occlude the blood vessel in an inflated state, the inflatable balloon being arranged at a distal end of the inflation sheath. The suction sheath has a tubular extension which extends beyond the distal end of the inflation sheath, the length of the extension being defined such that a distal tip of the extension is placed downstream the ophthalmic segment of the internal carotid artery when the distal end of the inflation sheath is placed upstream the ophthalmic segment.

In accordance with this aspect, a catheter is provided that may allow to extract, e.g. aspirate or remove, thrombotic material from a region downstream of the ophthalmic segment, which may be a particularly delicate region of a brain blood vessel, and occlude the internal carotid artery in an area of the internal carotid artery outside of the subarachnoid space. Examples of areas outside the subarachnoid space may be the cavernous or the intrapetrous segment of the internal carotid artery. If a secondary lesion of the wall of the internal carotid would happen, e.g. a rupture, in those cavernous or intrapetrous segments, that lesion would rarely produce an intracranial bleeding on one hand. On the other hand, the lesion would prevent the passage of blood through the internal carotid and this would probably be compensated intracranially by the blood from the Circle of Willis. The blood from the Circle of Willis might feed the brain, at least partially, and this could compensate for the prevention of the passage of blood through the internal carotid owing to a lesion without clinical consequences.

Furthermore, a lesion of the wall of the internal carotid artery upstream the ophthalmic segment may not pose as high a risk as an injury downstream of the ophthalmic segment. A downstream injury of the ophthalmic segment may be life-threatening or cause more severe damage. More severe damage may be related to the patient's personality, e.g. loss of vision, speech, hearing, partial or full mobility of the body, etc.

Thus, occluding the internal carotid upstream the ophthalmic segment may mean occluding the internal carotid in a safer area than downstream the ophthalmic segment.

In accordance with that aspect, a proximal occlusion with the inflatable balloon and a distal aspiration or withdrawal of the thrombus may be achieved by the herein disclosed catheter in use.

In accordance with that aspect, an upstream occlusion with the inflatable balloon and a downstream aspiration or withdrawal of the thrombus may be achieved with the herein disclosed catheter in use.

The extension may protrude from the inflation sheath in the distal direction or towards the thrombotic material or tissue in use. The extension may extend beyond the distal end of the inflation sheath following a direction of a longitudinal axis of the catheter. As the suction sheath and inflation sheath may be relatively coaxial, the extension may protrude from the distal end of the inflation sheath following a direction of the longitudinal axis of suction sheath and inflation sheath.

The thrombotic material may be a so-called soft thrombus, particularly a relatively recent soft thrombus.

The tubular extension may have substantially the same inner cross-section as the suction sheath. Substantially the same inner cross-section may be related to the size and/or shape.

The tubular extension may have substantially a different cross-section from the suction sheath. Substantially a different inner cross-section may be related to the size and/or shape.

The inflation sheath may be arranged around the suction sheath at least partially.

The ophthalmic segment comprises a region of the internal carotid artery where ophthalmic artery arises. The ophthalmic artery emerges from the internal carotid artery downstream the carotid siphon.

In an example, the length of the extension may be defined such that a distal tip of the extension is placed in the middle cerebral artery when the distal end of the inflation sheath is placed in the petrous part or the cavernous part of the internal carotid artery. This way the thrombotic material may be removed or extracted from the middle cerebral artery through the distal tip of the extension. The balloon may be inflated in the petrous part or the cavernous part.

In relation to the above, a particularly delicate area of a brain blood vessel may be the middle cerebral artery and a reinforced area of the internal carotid artery may be the cavernous or petrous part of the internal carotid artery.

In some examples, the length of the extension may be defined such that a distal tip of the extension is placed in the middle cerebral artery when the balloon is arranged to occlude the petrous or cavernous part of the internal carotid artery.

In a further example, the length of the extension is within the range of 25 mm to 60 mm, specifically 45 to 55 mm. An extension having a length within those ranges may allow to remove thrombotic material from downstream the ophthalmic segment when upstream the ophthalmic segment may be occluded owing to the inflatable balloon.

An extension having a length within those ranges may allow to remove thrombotic material from the middle cerebral artery when the internal carotid artery may be occluded in the cavernous or petrous part owing to the inflatable balloon.

The length of the extension according to any of the examples disclosed herein may allow removal of the thrombus from a significantly delicate region while temporarily occluding upstream blood circulation in a relatively more protected area of the head circulatory system.

The expression distal as used herein may be understood to mean the area farthest from the practitioner or the area which is to be closer to the clot in use. For example, a distal end of a part is intended to be closer to a thrombotic material in use than a proximal end.

The expression proximal as used herein may be understood to mean the area closest to the practitioner or the area which is to be farthest to the clot in use. For example, a proximal end of a part is intended to be farther to a thrombotic material in use than a distal end.

The expression distal as used herein may be understood to mean intended to be closer to the thrombotic material or tissue in use.

The expression proximal as used herein may be understood to mean intended to be closer to the introduction point in a blood vessel in use.

The expressions upstream and downstream as used herein may be related to the direction of the flow of blood through a human blood vessel/s. For instance, the blood flows from a region upstream the ophthalmic segment to a region downstream the ophthalmic segment. Or the blood flows from the internal carotid artery to the middle cerebral artery.

For the purposes of the present disclosure, the expression "the inflatable balloon being arranged at a distal end of the inflation sheath" may be understood to mean that the balloon may surround at least partially the distal end of the inflation sheath in a deployed or inflated status. In some examples, the balloon may fully surround the distal end of the inflation sheath in a deployed or inflated status.

The term "head blood vessel" may refer to a single blood vessel, e.g. the internal carotid artery or to a set of blood vessels in fluid communication with each other that may define a blood pathway, e.g. the internal carotid artery and the middle cerebral artery. The set of blood vessels may comprise a first and a second blood vessel in fluid communication with each other.

In the present disclosure, any size or shape may be considered based on an average size or shape of the body of an adult person.

BRIEF DESCRIPTION OF THE DRAWINGS

Non-limiting examples of the present disclosure will be described in the following, with reference to the appended drawings, in which.

DETAILED DESCRIPTION OF EXAMPLES

Figure 9:
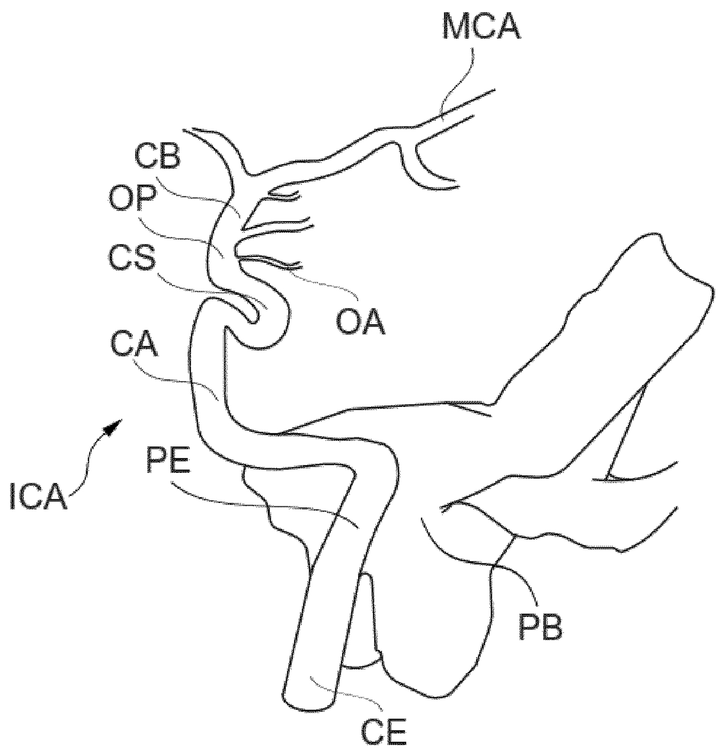
FIG. 9 schematically illustrates examples of blood vessels.

FIG. 9 schematically illustrates examples of blood vessels. Particularly, some parts of the internal carotid artery ICA and the middle cerebral artery MCA of a human body. In the present disclosure it is considered that the internal carotid artery ICA comprises, inter alia, the following segments or parts: cervical CE, petrous PE, cavernous CA, carotid siphon CS, ophthalmic OP and cerebral CB. In FIG. 9, the petrous bone PB has been schematically illustrated as well.

Figure 1:
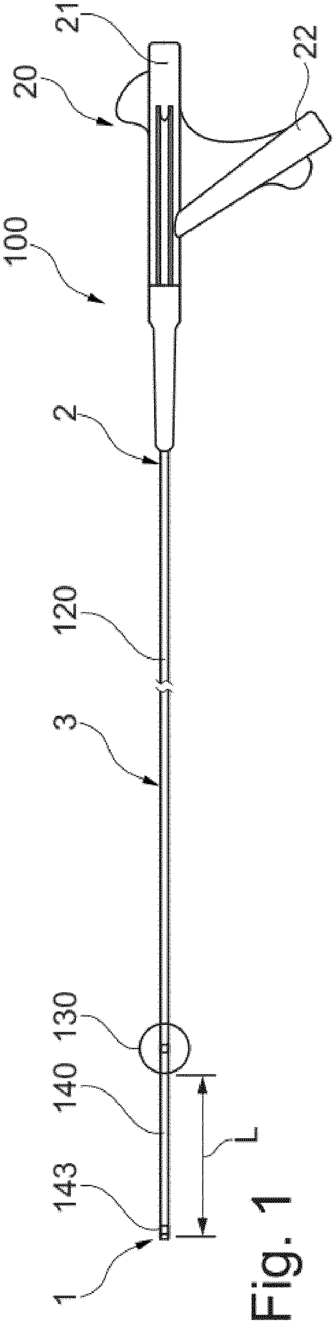
FIG. 1 schematically illustrates an example of a system for retrieving thrombotic material from a blood vessel.

FIG. 1 schematically illustrates an example of a system 100 for retrieving thrombotic material from a blood vessel. The system 100 comprises a catheter 3 to be introduced through a blood vessel of a human being. The catheter 3 may be according to any herein disclosed examples. The system 100 presents a generally elongated construction having a distal side 1 and a proximal side 2. The parts of the present disclosure may be referred to the distal or proximal side for the sake of convenience.

The catheter 3 may be introduced into the patient's body at a suitable point through a puncture (not shown) in order to access the circulatory system, e.g. a peripheral or neurovascular artery. The catheter 3 may be advanced to the area of the circulatory system where the thrombotic material to be removed is supposed to be located. This area may be referred as a target site. The thrombotic material may be located in the head area, particularly in a blood vessel in the head. The distal side 1 is intended to be the first part to be introduced into the patient's body and is the part of the catheter 3 that is intended to be closest to the thrombotic material to be removed.

To reach the target area, the catheter 3 may go coaxially through a guiding catheter (not shown). To assist in the distal navigation, a microcatheter and a guidewire may be arranged inside the catheter 3.

The most distal part of the catheter 3 may end in a rounded, atraumatic tip to avoid or at least reduce damage to blood vessels during advancement. The distal part of the catheter may be coated with a hydrophilic coating, which may aid in navigating the catheter through circuitous routes in the circulatory system.

The catheter may be made of a suitable material or may have a configuration that allows it to adapt to the shape of the blood vessels. At least the material of the catheter 3 intended to be in contact with the blood vessel may be biocompatible.

The system 100 of FIG. 1 has a hub 20 for receiving fittings. Hub 20 may be a female Luer-lock connector that may mate with male Luer-lock fittings not shown. Male Luer-lock fittings may comprise infusion or withdrawal syringes or hemostasis keys. The male and female Luer-lock is a standardized system of small-scale fluid fittings used for making leak-free connections between a male fitting and its mating female part on medical and laboratory devices.

The hub 20 of the example in FIG. 1 is "Y" shaped and has two input ports 21, 22. The shape and number of ports may vary depending on the case. In the illustrated system, the hub has a side port 22 and a straight port 21. The side port 22 may allow diluted contrast to enter for inflation and deflation of an inflatable balloon 130 of the catheter 3. The straight port 21 may be configured to allow passage of devices, such as microcatheters, stents, guidewires, retriever devices, liquids, aspiration, etc.

In an example, the effective length of the catheter may be, but not limited to, 125 cm. The overall length of the catheter may be, but not limited to, 132 cm. The external diameter of the catheter may be compatible with 6 F to 8 F introducer sheaths. The latter may mean that the catheter 3 may pass through the interior of such introducer sheaths.

Figure 2:
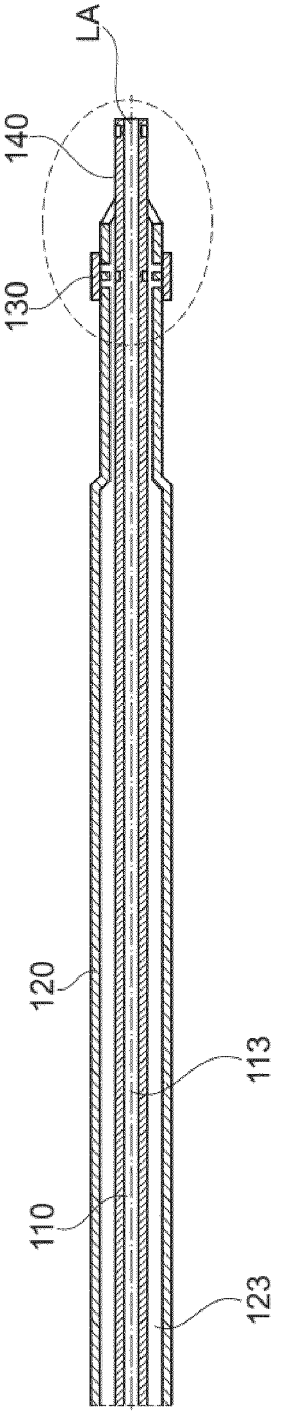
FIG. 2 schematically illustrates a partial and cross-sectional view of a suction sheath and an inflation sheath of a catheter of the system of FIG. 1.
Figure 3:
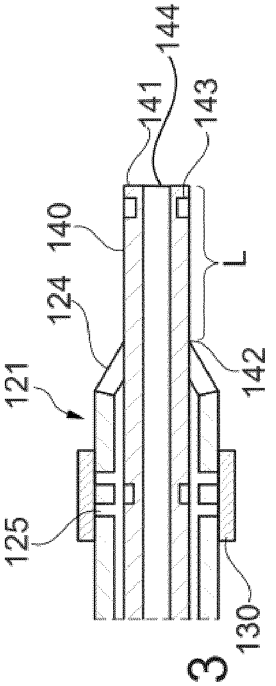
FIG. 3 schematically illustrates a detail of the distal end of the suction sheath and inflation sheath according to the example of the FIG. 2.

FIG. 2 schematically illustrates a partial and cross-sectional view of a suction sheath and an inflation sheath of the catheter of the system of FIG. 1, and FIG. 3 schematically illustrates a detail of the distal end of the suction sheath and inflation sheath according to the example of the FIG. 2.

As previously mentioned, an aspect of the present disclosure relates to a catheter 3 for extracting thrombotic material 400 from a head blood vessel 200. The catheter 3 comprises a suction sheath 110 to extract the thrombotic material 400 from the distal side 1 to the proximal side 2 of the catheter 3. The catheter also comprises an inflation sheath 120 to feed an inflatable balloon 130 to occlude the blood vessel 200 in an inflated state. The inflatable balloon 130 is arranged at a distal end 121 of the inflation sheath.

The suction sheath 110 has a tubular extension 140 which extends beyond a distal end 121 of the inflation sheath. The length of the extension L is defined such that a distal tip of the extension 141 is placed downstream 201 the ophthalmic segment OP of the internal carotid artery when the distal end 121 of the inflation sheath is placed upstream 202 the ophthalmic segment OP.

According to some examples, the length of the extension L may be defined such that a distal tip 141 of the extension is placed in the middle cerebral artery when the distal end 121 of the inflation sheath is placed in the petrous part PE or the cavernous part CA of the internal carotid artery. This way, the distal tip 141 of the extension may be placed downstream the ophthalmic segment OP when the distal end of the inflation sheath is placed upstream the ophthalmic segment OP.

In some examples, the length of the extension L may be defined such that a distal tip 141 of the extension is placed in the middle cerebral artery when the balloon 130 is arranged to occlude the petrous or cavernous part of the internal carotid artery. The petrous or cavernous part is placed upstream the ophthalmic segment. The petrous or cavernous part may provide support to the walls of the blood vessel when the balloon 130 is inflated to occlude the blood vessel.

In an example, the length of the extension L may be within the range of 25 mm to 60 mm, specifically 45 to 55 mm. Those figures may allow that a distal tip 141 of the extension to be placed downstream the ophthalmic segment OP, for instance in the middle cerebral artery when the distal end 121 of the inflation sheath is placed in the cavernous or petrous part of the internal carotid artery.

The length of the extension L may be enough to be arranged along the carotid siphon in use.

In the examples of FIGS. 2 and 3, the inflation sheath 120 is arranged around the suction sheath 110 so that the inflation sheath 120 and the suction sheath 110 are coaxially arranged. In FIGS. 2 and 3, a longitudinal axis LA of the catheter 3 has been illustrated. The feature coaxially arranged may be related to a longitudinal axis LA of the catheter 3 as illustrated in FIG. 2.

In an example, the inflation sheath 120 may surround the suction sheath 110 at least partially. In some non-illustrated examples, the inflation sheath 120 and the suction sheath 110 may be non-coaxially arranged and within a third covering tube.

In one example, the suction sheath 110 may have several stiffness transitions along its length, for example ten transitions. The proximal end may be stiffer than the distal end.

The extension 140 may have different mechanical features than the rest of the suction sheath 110. By way of non-limiting example, the extension 140 may be more flexible than the rest of the suction sheath 110. The extension 140 is not surrounded by the inflation sheath 120 and may be better adapted to the shape of particularly delicate blood vessels such as the middle cerebral artery and/or the region downstream of the ophthalmic segment.

In some examples, the inflation sheath 120 may have several stiffness transitions along its length, for example three transitions. The proximal end may be stiffer than the distal end.

The number and location of transitions in both the suction sheath and the inflation sheath may be varied depending on the case.

The inflation sheath 120 and the suction sheath 110 may be detachably joined with each other. The inflation sheath 120 and the suction sheath 110 may be arranged in such a way that there is substantially no relative displacement between them in the direction of the longitudinal axis and/or relative rotation about the longitudinal axis LA. The inflation sheath 120 and the suction sheath 110 may be fixedly arranged relative to each other.

According to examples, the inflation sheath 120 may comprise a tubular body. In an example the inflation sheath 120 may have an outer diameter of 2.13 mm. This diameter and/or shape may vary depending on the case.

The tubular body of the inflation sheath 120 may be made of a reinforced material, e.g. forming a braid, at least partially. This provides a relatively robust configuration while allowing the outer contour of the inflation sheath 120 to conform to the shape of the blood vessel. Examples of suitable materials for the inflation sheath may comprise stainless steel, e.g. stainless steel 304V, nitinol, textiles, fibers or high strength polymers.

A suction lumen 113 may be defined within the suction sheath 110. The suction lumen 113 may be further defined within the extension 140 of the suction sheath. The suction lumen may have a cross-section with a shape and size substantially the same in the suction sheath 110 and the extension 140. In some examples, the suction lumen may have a cross-section with a shape and/or size that may vary from that one of the suction sheath 110.

The suction sheath 110 may comprise a tubular body. In examples the tubular body of the inflation sheath 120 may surround at least partially and concentrically the tubular body of the suction sheath 110.

The tubular body of the suction sheath 110 may have a reinforced configuration. The tubular body of the suction sheath 110 may comprise a braid or a coil or a fiber-like structure. The tubular body of the suction sheath 110 may comprise a coil. This coil may be made of nitinol or any other suitable material having elastic properties. The coiled configuration or structure may allow the suction sheath to adapt its outline to the shape of the blood vessel while having adequate mechanical strength. Examples of suitable materials for the suction sheath may comprise stainless steel, nitinol, textiles, fibers or high strength polymers.

The suction lumen 113 may be configured as a kind of pathway that allows thrombotic material to be driven from the distal end to the proximal end of the catheter 3. Thrombotic material or thrombus may be driven through the suction lumen by suction and/or by mechanical extraction.

In an example to remove the thrombus by suction, an adequate vacuum may be generated within the suction lumen that may, at least partially, absorb the thrombus from the blood vessel. A vacuum source may be connected to the proximal end of the catheter 3 to provide vacuum in the suction lumen 3. The vacuum source may be in fluid communication with hub 20.

In an example to remove the thrombus by mechanical extraction, the suction lumen may allow passage of devices and tools to and from the area of the head blood vessel where the thrombotic material is located. Examples of devices that may be employed to remove thrombotic material will be described in the present disclosure.

An inflation lumen 123 may be defined between the inflation sheath 120 and the suction sheath 110. The inflation lumen 123 may be configured as a path for a fluid, employed to inflate or deflate the inflatable balloon 130. The fluid passage may be in the direction of the distal end of the catheter when the balloon 130 is to be inflated or in the direction of the proximal end of the catheter when the balloon 130 is to be deflated. An inflation device, e.g. a syringe, may be connected at a proximal end of the catheter to feed the inflation lumen 123 with fluid.

The catheter may comprise an inflation hole 125 substantially arranged at the distal end of the inflation sheath 121 such that the inside of the balloon 130 may be in fluid communication with the inflation lumen 123. The number of inflation holes 125 may vary from case to case. The hole or holes 125 may be arranged defining a spiral or a straight line. Thanks to the inflation orifice 125 an amount of fluid may enter or leave the inflatable balloon 130 from or to the inflation lumen 123. An inflatable balloon 130 may be fed by one or more inflation holes 125.

In an example, the inflation volume of the inflatable balloon may be within the range of about 0.5 ml and 2.0 ml. The number of balloons 130 may vary depending on the case.

In examples, the extension 140 of the suction sheath may comprise a tubular body. The tubular body of the extension 140 of the suction sheath may have a reinforced configuration in a shape of a braid, a coil or a fiber-like structure. The tubular body of the extension 140 may comprise a coil. This way, the behaviour of the extension 140 is substantially the same as the suction sheath. The extension may be adapted to the relatively complex shape of the head arteries, e.g. the carotid siphon CS, and maintain adequate mechanical strength. Examples of suitable materials for the extension may comprise stainless steel, nitinol, textiles, fibers and high strength polymers or nitinol.

In examples, the extension 140 may have an inner diameter of at least 1.45 mm. The extension 140 may have an outer diameter of at least 1.60 mm. However, those details may vary depending on the shape and size of the example.

In some examples, the inner diameter of the extension may be within the range of about 1.45 and 1.70 mm. In examples, the extension 140 may have an outer diameter within the range of about 1.60 and 2.13 mm.

The suction sheath 110 may be integrally made with the extension 140 or both parts may be attached to each other.

As shown in the example of FIG. 3, the distal tip 141 of the extension has an opening 144 to receive the thrombotic material. The opening 144 may be a mouth of the tubular body of the extension.

Following with the example of FIGS. 2-3, it can be seen that the inflation sheath 120 has a tapered end 124 to the distal side 1. The tapered end 124 may help to introduce the catheter 3 through the blood vessels. The tapered end 124 may be defined between an outer face of the inflation sheath 120 and the proximal tip 142 of the extension 140.

Figure 4A:
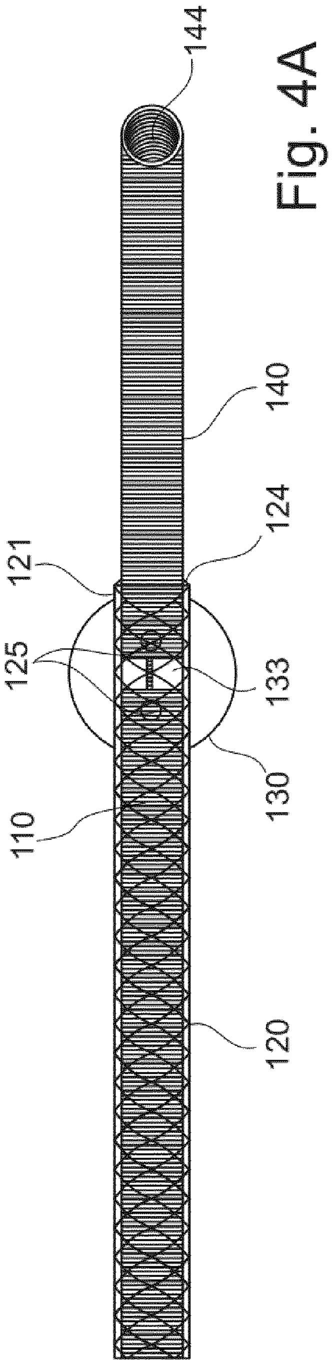
FIGS. 4A and 4B schematically illustrate partial views of the distal end of the catheter from different perspectives according to an example.
Figure 4B:
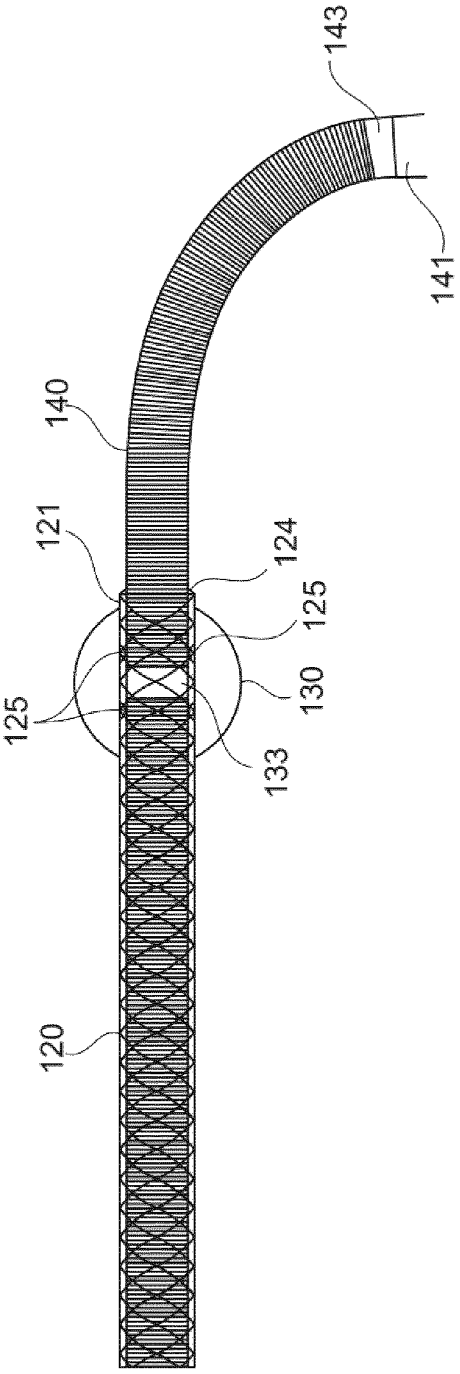

FIGS. 4A and 4B schematically illustrates partial views of the distal end of the catheter from different perspectives according to an example. Some hidden elements have been illustrated in these figures for the sake of clarity. This way, the structure of the elements according to an example can be seen. As shown in FIGS. 4A, 4B, the suction sheath 110, the inflation sheath 120 and the extension 140 may adopt a particular shape over at least a portion of their length. This particular shape may correspond to a shape of a blood vessel.

In the examples in FIGS. 3 and 4B, it can be seen that the extension 140 of the suction sheath comprises a first radiopaque marker element 143. The first radiopaque marker element 143 may be arranged at the distal tip 141. It can be seen in FIGS. 4A and 4B, that the inflatable balloon 130 comprises a second radiopaque marker element 133. Although an example has been illustrated having first and second radiopaque elements, examples not illustrated in which only one or neither of the radiopaque elements is present are envisaged.

Figure 5:
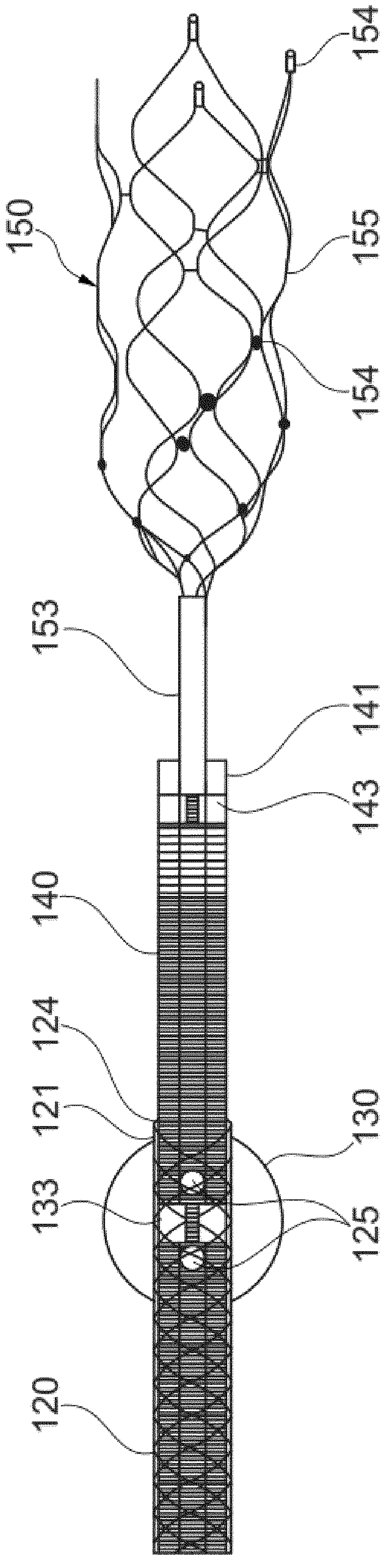
FIG. 5 schematically illustrates a partial view of the distal end of the catheter and a deployable mesh according to an example.

FIG. 5 schematically illustrates a partial view of the distal end of the catheter and a deployable mesh according to an example. The deployable mesh may be an example of mechanical retriever or retrieving device. Although the example of FIG. 5 illustrates a catheter 3 in a generally straight state, the overall shape of the catheter 3 may vary to adopt the overall shape of the blood vessel.

The catheter 3 may comprise devices for mechanical extraction of the thrombotic material, as above mentioned. In one example, the catheter 3 may comprise the deployable mesh 150 to pass through the suction lumen 113 in a folded position and to encapsulate, at least partially, the thrombotic material 400 in a deployed position. The deployable mesh 150 may be arranged inside a microcatheter 153 to be driven through the suction lumen 113. An example of microcatheter 153 has been illustrated in FIG. 5. The microcatheter 153 and the mesh may be introduced into the suction lumen through the straight port 21 of the hub 20 of FIG. 1. The deployable mesh 150 may comprise a number of wires 155 interconnected to each other to form a net. The deployable mesh 150 may be a stent retriever.

Although an example of deployable mesh 150 has been described in the present disclosure, the user may implement other examples of mechanical retrievers that may vary in shape, material or components. The mechanical retrievers may capture or encapsulate the thrombotic material to be removed from the blood vessel. Non-illustrated examples of mechanical retrievers may pass through the suction lumen as well.

According to some examples the catheter 3 may comprise a guidewire, not illustrated for the sake of clarity, to guide a displacement of the catheter 3 through the blood vessel 200 along with the microcatheter 153. The diameter of the guidewire may be chosen to pass through the microcatheter 153.

Figure 6:
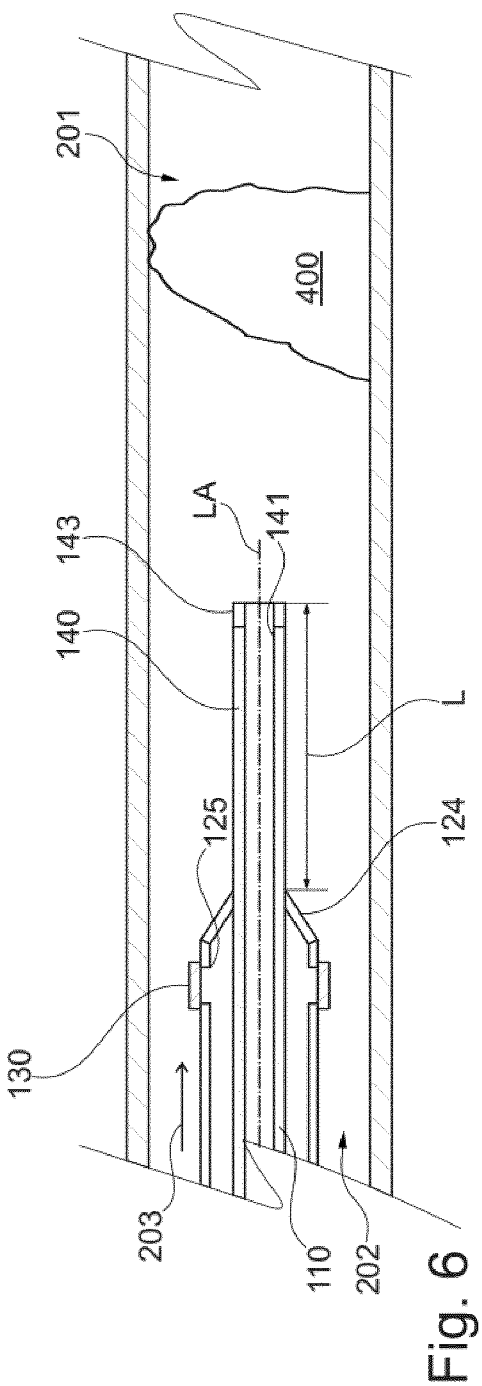
FIG. 6 schematically illustrates a partial view of the distal end of the catheter of FIG. 2 within a portion of a blood vessel.
Figure 7:
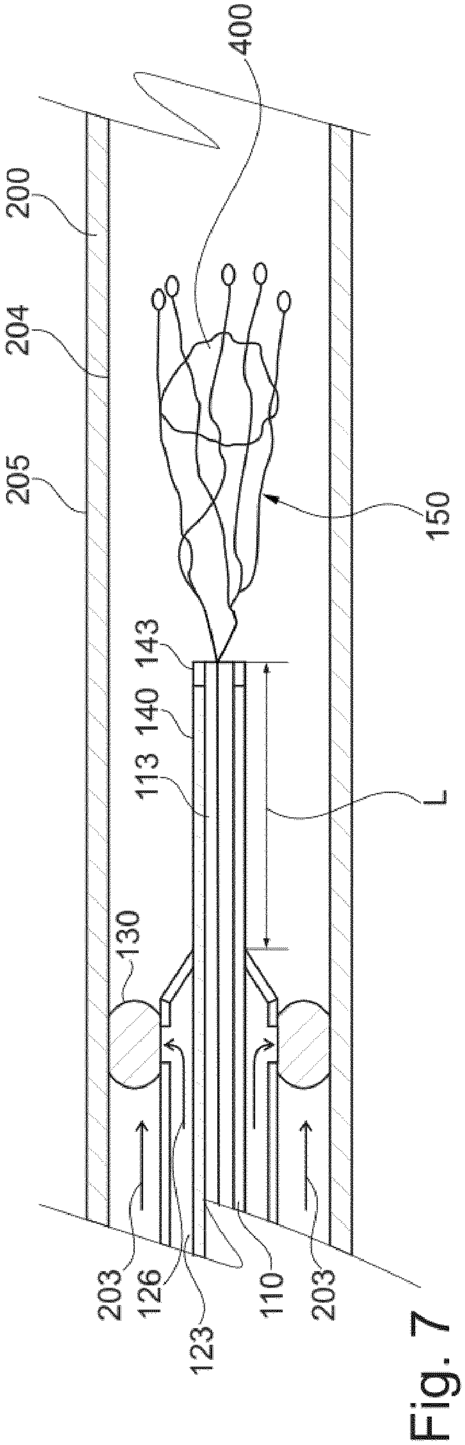
FIG. 7 schematically illustrates a partial view of the distal end of the catheter of FIG. 6 having a mechanical retriever in a deployed status.
Figure 8:
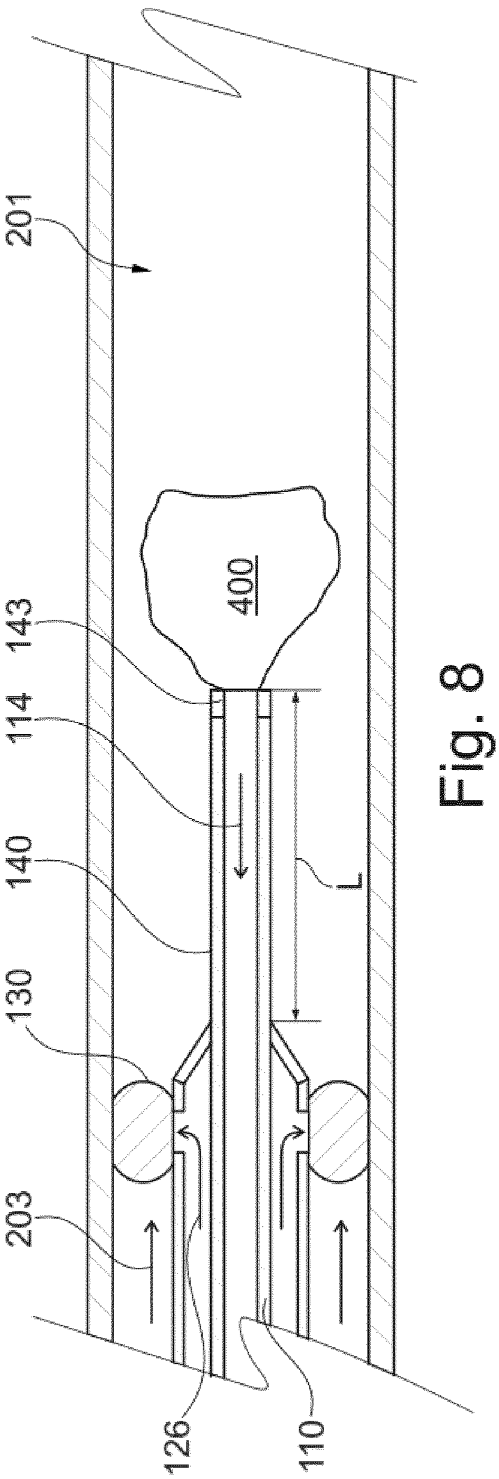
FIG. 8 schematically illustrates a partial view of the distal end of the catheter of FIG. 6 aspirating thrombotic material.
Figure 10:
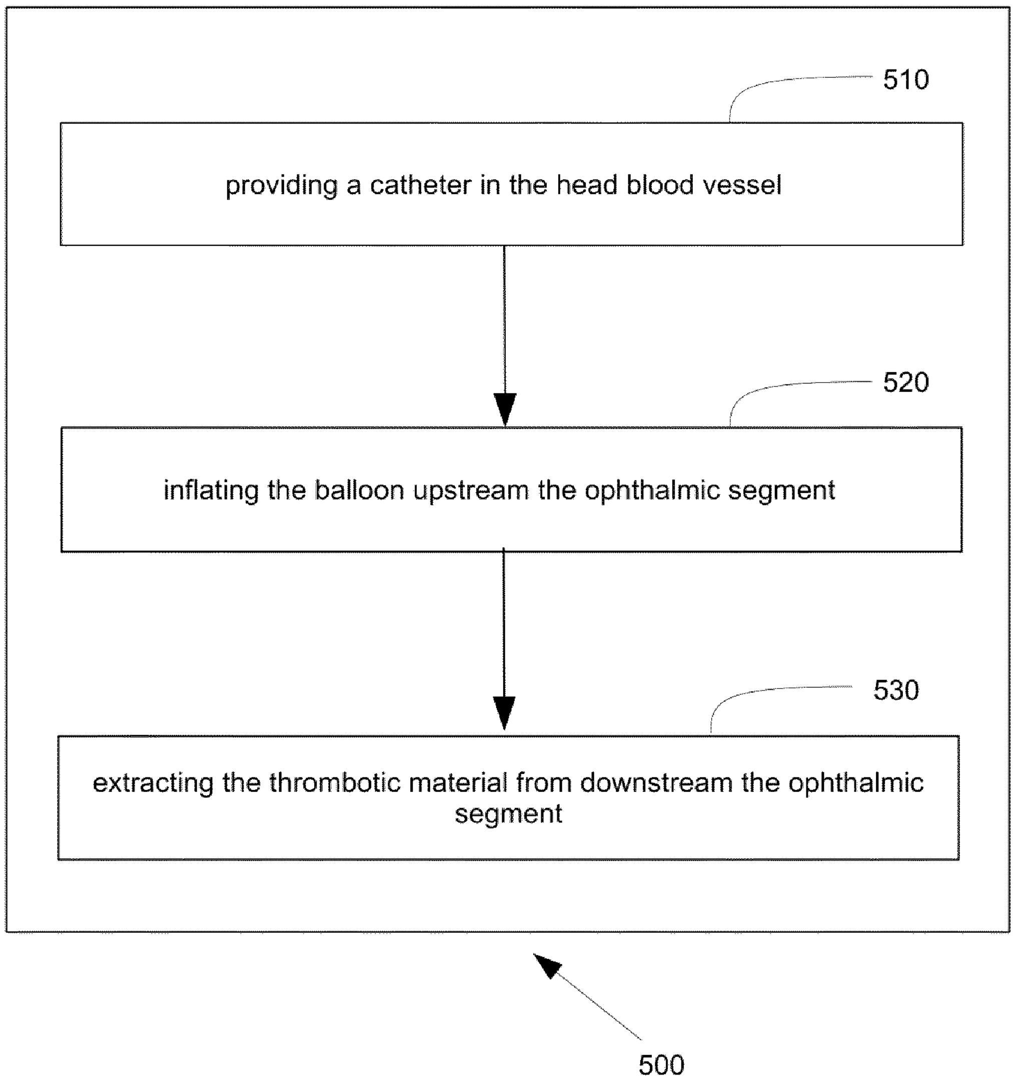
FIG. 10 is a block diagram of an example of a method of the present disclosure.

Examples of methods for the extraction of thrombotic material according to the present disclosure will be described below. Such methods may be performed with catheters of the herein described examples. The examples of methods are described in relation to the FIGS. 6-8. FIG. 6 schematically illustrates a partial view of the distal end of the catheter of FIG. 2 within a portion of a blood vessel. FIG. 7 schematically illustrates a partial view of the distal end of the catheter of FIG. 6 having a mechanical retriever in a deployed status. And FIG. 8 schematically illustrates a partial view of the distal end of the catheter of FIG. 6 aspirating thrombotic material. FIG. 10 is a block diagram of an example of a method of the present disclosure.

According to an aspect of the present disclosure a method 500 for extracting thrombotic material from a head blood vessel is disclosed. The method 500 comprises:

- providing a catheter as herein disclosed in the head blood vessel 510 so that the distal end of the suction sheath is placed downstream the ophthalmic segment OP of the internal carotid artery when the distal end of the inflation sheath is placed upstream the ophthalmic segment OP. A guidewire along with a microcatheter may be arranged inside the catheter 3, and the catheter 3 having the guidewire and the microcatheter may be introduced through the patient's circulatory system until they reach the target site, i.e. an area close to or involving the thrombotic material 400 to be removed. At least a distal part of the catheter 3 may remain in the target vessel 200. FIG. 6 shows a schematic representation of how the catheter 3 may be positioned within or inside the blood vessel 200 to remove the thrombus 400. In one example, the distal tip of the extension 141 may be positioned downstream of the ophthalmic segment OP while the distal end of the inflation sheath 121 may be positioned upstream of the ophthalmic segment OP. In FIG. 6 the inflatable balloon 130 is in its retracted or deflated position, so that blood flow 203 continues to flow through the blood vessel 200;
- inflating the balloon upstream the ophthalmic segment 520. In FIGS. 7 and 8, the balloon 130 is fed with a fluid 126. The fluid 126 flows through the inflation lumen 123 and exits through the inflation hole 125 into the interior of the balloon 130. The catheter 3 may be positioned in the patient's body so that the distal end 121 of the inflation sheath and thus the balloon 130 is positioned substantially in an area upstream the ophthalmic segment OP. As more fluid 126 enters the balloon 130, the volume of the balloon 130 may increase and more occlusion may be exerted on the blood vessel 200, particularly on the inner face 204 of the vessel 200. The flow of blood 203 has been temporarily interrupted by the blocking action exerted by the inflated balloon 130;
- extracting the thrombotic material from downstream the ophthalmic segment 530. Thrombotic material 400 may be removed in different ways. FIG. 7 illustrates an example of the mechanical removal of thrombotic material using the deployable mesh 150. FIG. 8 illustrates an example of removal by suction or aspiration. In any case, the thrombus or part of the thrombus 400 may be displaced along the suction lumen 113 to the proximal end of the catheter following direction depicted by arrow 114. In the example of suction, the thrombotic material may be aspirated or suctioned, for example thanks to a vacuum generated by a vacuum source in fluid communication with the hub 20. In the example of mechanical retrieval, the retriever may be driven from the distal end of the catheter 3 by a driving device connected to the hub 20 or even by the user. The presence of the extension 140 with a length L as defined in the present disclosure may allow making a distal removal of the thrombus with a proximal blockage of blood flow 203.

In some examples of the method 500, providing a catheter as herein disclosed in the head blood vessel 510 so that the distal end of the suction sheath is placed downstream the ophthalmic segment OP of the internal carotid artery when the distal end of the inflation sheath is placed upstream the ophthalmic segment OP, may comprise providing the catheter so that the distal tip of the extension is placed in the middle cerebral artery when the distal end of the inflation sheath is placed in the petrous part or the cavernous part of the internal carotid artery;

- wherein inflating the balloon upstream the ophthalmic segment may comprise inflating the balloon in the petrous part PE or the cavernous part CA of the internal carotid artery;
- wherein extracting the thrombotic material from downstream the ophthalmic segment OP may comprise suctioning the thrombotic material from the middle cerebral artery MCA.

According to some examples of the method 500, the distal tip of the extension may be placed in the middle cerebral artery when the balloon 130 is arranged to occlude the petrous or cavernous part of the internal carotid artery. The balloon 130 may be arranged with respect to the inflation sheath 120 to block the internal carotid artery in such a way.

In examples, the method 500 may comprise:

- deploying a deployable mesh 150 to encapsulate at least partially the thrombotic material 400. The practitioner may control the operation of the deployed mesh 150 through the hub 20;
- dislodging the encapsulated thrombotic material before suctioning the thrombotic material. The deployable mesh 150 may help to remove the thrombotic material 400 which may be suctioned through the suction lumen. The thrombotic material 400 may comprise at least a part of a soft thrombus.

In some examples, the method may comprise:

passing a microcatheter through the extension of the suction sheath to drive the deployable mesh 150. The microcatheter may pass along the suction lumen from the hub 20 to the distal tip 141 of the extension 140. The practitioner may control the motion of the microcatheter through the hub 20.

For reasons of completeness, various aspects of the present disclosure are set out in the following numbered clauses:

Clause 1. A catheter for extracting thrombotic material from a head blood vessel comprising:
- a suction sheath to extract the thrombotic material from a distal side to a proximal side of the catheter;
- an inflation sheath to feed an inflatable balloon to occlude the blood vessel in an inflated state, the inflatable balloon being arranged at a distal end of the inflation sheath;
- wherein the suction sheath has a tubular extension which extends beyond the distal end of the inflation sheath, the length of the extension being defined such that a distal tip of the extension is placed downstream the ophthalmic segment of the internal carotid artery when the distal end of the inflation sheath is placed upstream the ophthalmic segment.

Clause 2. The catheter according to clause 1, wherein the length of the extension is defined such that a distal tip of the extension is placed in the middle cerebral artery when the distal end of the inflation sheath is placed in the petrous part or the cavernous part of the internal carotid artery.

Clause 3. The catheter according to clause 1, wherein the length of the extension is defined such that a distal tip of the extension is placed in the middle cerebral artery when the balloon is arranged to occlude the petrous or cavernous part of the internal carotid artery.

Clause 4. The catheter according to any of clauses 1-3, wherein the length of the extension is within the range of 25 mm to 60 mm, specifically 45 to 55 mm.

Clause 5. The catheter according to any of clauses 1-4, wherein the inflation sheath is arranged around the suction sheath so that the inflation sheath and the suction sheath are coaxially arranged.

Clause 6. The catheter according to any of clauses 1-5, wherein a suction lumen is defined within the suction sheath.

Clause 7. The catheter according to clause 6, wherein the suction lumen is further defined within the extension of the suction sheath.

Clause 8. The catheter according to any of clauses 1-7, wherein an inflation lumen is defined between the inflation sheath and the suction sheath.

Clause 9. The catheter according to clause 8, comprising an inflation hole substantially arranged at the distal end of the inflation sheath such that the inside of the balloon is in fluid communication with the inflation lumen.

Clause 10. The catheter according to any of clauses 1-9, wherein the inflatable balloon is arranged at the distal end of the inflation sheath.

Clause 11. The catheter according to any of clauses 1-10, wherein the extension of the suction sheath comprises a tubular body.

Clause 12. The catheter according to clause 11, wherein the tubular body of the extension of the suction sheath has a reinforced configuration, preferably a coiled configuration.

Clause 13. The catheter according to any of clauses 1-12, wherein the extension of the suction sheath comprises a first radiopaque marker element, and wherein the inflatable balloon comprises a second radiopaque marker element.

Clause 14. The catheter according to any of clauses 1-13, wherein the distal tip of the extension has an opening to receive the thrombotic material.

Clause 15. The catheter according to any of clauses 6-7 comprising a deployable mesh to pass through the suction lumen in a folded position and to encapsulate the thrombotic material in a deployed position.

Clause 16. A method for extracting thrombotic material from a head blood vessel comprising:
- providing a catheter according to any of clauses 1-15 in the head blood vessel so that the distal end of the suction sheath is placed downstream the ophthalmic segment of the internal carotid artery when the distal end of the inflation sheath is placed upstream the ophthalmic segment;
- inflating the balloon upstream the ophthalmic segment;
- extracting the thrombotic material from downstream the ophthalmic segment.

Clause 17. The method according to clause 16, wherein providing a catheter in the head blood vessel so that the distal end of the suction sheath is placed downstream the ophthalmic segment of the internal carotid artery when the distal end of the inflation sheath is placed upstream the ophthalmic segment, comprise providing the catheter so that the distal tip of the extension is placed in the middle cerebral artery when the distal end of the inflation sheath is placed in the petrous part or the cavernous part of the internal carotid artery;
- wherein inflating the balloon upstream the ophthalmic segment comprises inflating the balloon in the petrous part or the cavernous part of the internal carotid artery;
- wherein extracting the thrombotic material from downstream the ophthalmic segment comprises suctioning the thrombotic material from the middle cerebral artery.

Clause 18. The method according to clause 16, wherein the distal tip of the extension is placed in the middle cerebral artery when the balloon is arranged to occlude the petrous or cavernous part of the internal carotid artery.

Clause 19. The method according to any of clauses 16-18, comprising:
- deploying a deployable mesh to encapsulate at least partially the thrombotic material;
- dislodging the encapsulated thrombotic material before extracting the thrombotic material.

Clause 20. The method according to clause 19, comprising:
- passing a microcatheter through the extension of the suction sheath to drive the deployable mesh.

Clause 21. A catheter for extracting thrombotic material from a head blood vessel comprising:
- a suction sheath to extract the thrombotic material from a distal side to a proximal side of the catheter;
- an inflation sheath to feed an inflatable balloon to occlude the blood vessel in an inflated state, the inflatable balloon being arranged at a distal end of the inflation sheath;
- wherein the suction sheath has a tubular extension which extends beyond the distal end of the inflation sheath, the length of the extension is defined such that a distal tip of the extension is placed in the middle cerebral artery when the distal end of the inflation sheath is placed in the petrous part or the cavernous part of the internal carotid artery.

Clause 22. A catheter for extracting thrombotic material from a head blood vessel comprising:

a suction sheath to extract the thrombotic material from a distal side to a proximal side of the catheter;

an inflation sheath to feed an inflatable balloon to occlude the blood vessel in an inflated state, the inflatable balloon being arranged at a distal end of the inflation sheath;

wherein the suction sheath has a tubular extension which extends beyond the distal end of the inflation sheath, the length of the extension is defined such that a distal tip of the extension is placed in the middle cerebral artery when the balloon is arranged to occlude the petrous or cavernous part of the internal carotid artery.

Clause 23. A catheter for extracting thrombotic material from a head blood vessel comprising:

a suction sheath to extract the thrombotic material from a distal side to a proximal side of the catheter;

an inflation sheath to feed an inflatable balloon to occlude the blood vessel in an inflated state, the inflatable balloon being arranged at a distal end of the inflation sheath;

wherein the suction sheath has a tubular extension which extends beyond the distal end of the inflation sheath, the length of the extension is defined within the range of 25 mm to 60 mm, specifically 45 to 55 mm.

Clause 24. A method for extracting thrombotic material from a head blood vessel comprising:

providing a catheter according to any of clauses 1-15 and 33-35 so that the distal tip of the extension is placed in the middle cerebral artery when the distal end of the inflation sheath is placed in the petrous part or the cavernous part of the internal carotid artery;

inflating the balloon in the petrous part or the cavernous part of the internal carotid artery;

extracting the thrombotic material from the middle cerebral artery.

Clause 25. A method for extracting thrombotic material from a head blood vessel comprising:

providing a catheter according to any of clauses 1-15 and 21-23 so that the distal tip of the extension is placed in the middle cerebral artery when the balloon is arranged to occlude the petrous or cavernous part of the internal carotid artery;

inflating the balloon in the petrous part or the cavernous part of the internal carotid artery;

extracting the thrombotic material from the middle cerebral artery.

Clause 26. A system for extracting thrombotic material from a head blood vessel comprising a catheter according to any of clauses 1-15 and 21-23, and a hub for receiving fittings.

Although only a number of examples have been disclosed herein, other alternatives, modifications, uses and/or equivalents thereof are possible. Furthermore, all possible combinations of the described examples are also covered. Thus, the scope of the present disclosure should not be limited by particular examples, but should be determined only by a fair reading of the claims that follow. If reference signs related to drawings are placed in parentheses in a claim, they are solely for attempting to increase the intelligibility of the claim, and shall not be construed as limiting the scope of the claim.

What is claimed is:

1. A catheter for extracting thrombotic material from a head blood vessel comprising:

a suction sheath to extract the thrombotic material from a distal side to a proximal side of the catheter;

an inflation sheath to feed an inflatable balloon to occlude the blood vessel in an inflated state, the inflatable balloon being arranged at a distal end of the inflation sheath;

wherein the suction sheath has a tubular extension which extends beyond the distal end of the inflation sheath, the length of the extension being defined such that a distal tip of the extension is placed downstream the ophthalmic segment of the internal carotid artery when the distal end of the inflation sheath is placed upstream the ophthalmic segment;

wherein the inflation sheath and the suction sheath are fixedly arranged relative to each other.

2. The catheter according to claim 1, wherein the suction sheath is integrally made with the extension.

3. The catheter according to claim 1, wherein the length of the extension is defined such that a distal tip of the extension is placed in the middle cerebral artery when the distal end of the inflation sheath is placed in the petrous part or the cavernous part of the internal carotid artery.

4. The catheter according to claim 1, wherein the length of the extension is defined such that a distal tip of the extension is placed in the middle cerebral artery when the balloon is arranged to occlude the petrous or cavernous part of the internal carotid artery.

5. The catheter according to claim 1, wherein the length of the extension is within the range of 25 mm to 60 mm, specifically 45 to 55 mm.

6. The catheter according to claim 1, wherein the inflation sheath is arranged around the suction sheath so that the inflation sheath and the suction sheath are coaxially arranged.

7. The catheter according to claim 1, wherein a suction lumen is defined within the suction sheath.

8. The catheter according to claim 7, wherein the suction lumen is further defined within the extension of the suction sheath.

9. The catheter according to claim 1, wherein the extension of the suction sheath comprises a tubular body.

10. The catheter according to claim 9, wherein the tubular body of the extension of the suction sheath has a reinforced configuration, preferably a braid or coil.

11. The catheter according to claim 9, wherein the extension has an inner diameter within the range of about 1.45 and 1.70 mm.

12. The catheter according to claim 9, wherein the extension has an outer diameter within the range of about 1.60 and 2.13 mm.

13. The catheter according to claim 1, wherein the extension of the suction sheath comprises a first radiopaque marker element.

14. The catheter according to claim 1, wherein the suction sheath comprises a tubular body.

15. The catheter according to claim 14, wherein the tubular body of the suction sheath has a reinforced configuration, particularly a coil or braid.

16. The catheter according to claim 1, wherein the distal tip of the extension has an opening to receive the thrombotic material.

17. The catheter according to claim 1, wherein the extension has different mechanical features than the rest of the suction sheath.

18. A method for extracting thrombotic material from a head blood vessel comprising: providing a catheter in the head blood vessel, the catheter comprising:

a suction sheath to extract the thrombotic material from a distal side to a proximal side of the catheter;

an inflation sheath to feed an inflatable balloon to occlude the blood vessel in an inflated state, the inflatable balloon being arranged at a distal end of the inflation sheath;

wherein the suction sheath has a tubular extension which extends beyond the distal end of the inflation sheath, the length of the extension being defined such that a distal tip of the extension is placed downstream the ophthalmic segment of the internal carotid artery when the distal end of the inflation sheath is placed upstream the ophthalmic segment;

wherein the distal end of the suction sheath is placed downstream the ophthalmic segment of the internal carotid artery when the distal end of the inflation sheath is placed upstream the ophthalmic segment;

inflating the balloon upstream the ophthalmic segment;

extracting the thrombotic material from downstream the ophthalmic segment;

wherein the inflation sheath and the suction sheath are fixedly arranged relative to each other.

19. A method for extracting thrombotic material from a head blood vessel comprising:

providing a catheter in the head blood vessel, the catheter comprising:

a suction sheath to extract the thrombotic material from a distal side to a proximal side of the catheter;

an inflation sheath to feed an inflatable balloon to occlude the blood vessel in an inflated state, the inflatable balloon being arranged at a distal end of the inflation sheath;

wherein the suction sheath has a tubular extension which extends beyond the distal end of the inflation sheath, the length of the extension being defined such that a distal tip of the extension is placed downstream the ophthalmic segment of the internal carotid artery when the distal end of the inflation sheath is placed upstream the ophthalmic segment;

wherein the distal tip of the extension is placed in the middle cerebral artery when the distal end of the inflation sheath is placed in the petrous part or the cavernous part of the internal carotid artery;

inflating the balloon in the petrous part or the cavernous part of the internal carotid artery;

extracting the thrombotic material from the middle cerebral artery;

wherein the inflation sheath and the suction sheath are fixedly arranged relative to each other.

* * * * *